United States Patent [19]

Korsgaard et al.

[11] Patent Number: 5,798,369

[45] Date of Patent: Aug. 25, 1998

[54] 2-PHENYL-3-AZOYLBENZOTHIOPHENE FOR LOWERING INTRAOCULAR PRESSURE

[75] Inventors: Niels Korsgaard, Værløse; John Römer, Copenhagen, both of Denmark

[73] Assignee: Novo Nordisk A/S, Bagsvaerd, Denmark

[21] Appl. No.: 888,707

[22] Filed: Jul. 7, 1997

[30] Foreign Application Priority Data

Jul. 12, 1996 [DK] Denmark .................. 0782/96

[51] Int. Cl.⁶ .................................. A61K 31/445
[52] U.S. Cl. ................................ 514/324; 514/913
[58] Field of Search ........................ 514/324, 913

[56] References Cited

U.S. PATENT DOCUMENTS 5,521,168  5/1996  Clark ........................ 514/170

*Primary Examiner*—Zohrem Fay
*Attorney, Agent, or Firm*—Steve T. Zelson; Elias J. Lombiris

[57] ABSTRACT

The present invention provides a novel use of a compound of formula I

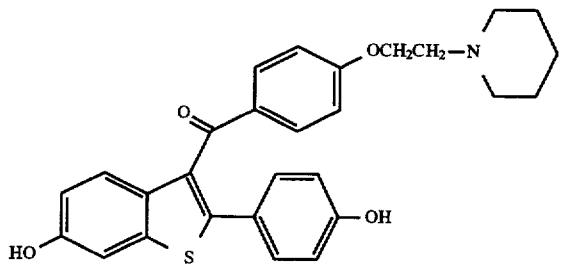

or a pharmaceutically and/or physiologically acceptable salt or solvate thereof for the manufacture of a pharmaceutical composition useful for lowering intraocular pressure.

7 Claims, No Drawings

2-PHENYL-3-AZOYLBENZOTHIOPHENE FOR LOWERING INTRAOCULAR PRESSURE

This application is a provisional of 60/031,243 filed Nov. 12, 1996.

FIELD OF THIS INVENTION

The present invention relates to the use of a compound of formula I or a pharmaceutically and/or physiologically acceptable salt or solvate thereof for the manufacture of a pharmaceutical composition for lowering intraocular pressure (IOP).

BACKGROUND OF THIS INVENTION

A number of disease states in which an increased intraocular pressure is the common denominator are included in the category of glaucoma. The pressure elevation results from an imbalance between aqueous inflow and outflow through the pupil, the trabecular meshwork and Schlemm's canal. Chronic or primary open-angle glaucoma, the most common of adult glaucomas, is asymptomatic and detected only by routine eye examination. It is associated with a relative obstruction to aqueous outflow through the trabecular meshwork and is of unknown cause. Glaucoma is characterized by progressive vision field loss due to nerve damage from the elevated intraocular pressure. It is an important cause of blindness world-wide and in the United States it occurs in 1 to 2 percent of people above age 60. Treatment includes the use of topical agents including cholinergic (pilocarpine, carbachol, echothiophate) or adrenergic agonists (epinephrine, dipivefrin) or antagonists e.g. beta adrenergic blockers (timolol, levobunanol, betaxol). Pilocarpine has been used for the treatment of glaucoma for over a hundred years. Pilocarpine is a muscarinic agonist that reduces resistance to aqueous humor outflow by causing contraction of the ciliary muscle, whereby the trabecular meshwork is pulled apart. Although pilocarpine is safe and effective it has side effects such as miosis (reduction of pupil size), which blurs the vision. It also has short duration of action, and therefore, has to be administered four-times a day, creating problems with patient compliance. Consequently, in spite of the treatment, there is a great risk for irreversible vision loss since pressure can increase dramatically during sleep and periods of irregular instillation. These facts has limited the use of pilocarpine and other muscarinics, and in the past decade other compounds which inhibits the aqueous humor formation have been the drugs of choice.

The I-form of epinephrine has adrenergic properties which in glaucoma acts via a reduction of the production of the aqueous humor by reducing blood flow to the ciliary body and is clinically useful. However, this compound causes mydriasis (i.e., an excessive dilation of the pupil) also blurring the vision. Also β-adrenergic antagonists reduces the formation of aqueous humor, but is contraindicated in patients with asthma and chronic obstructive lung diseases and can cause cardiac dysrythmias.

Recently it has been shown that prostaglandin $F_{2\alpha}$ lowers intraocular pressure probably by increasing the uveoscleral outflow, i.e. the unconventional drainage route of the eye, comprising only 5–10% of the normal outflow system. However, clinical studies have indicated that this prostaglandin increases the pigmentation of the iris. The consequences of this observation for the frequency of intraocular melanomas are still uncertain.

None of these treatments aim against the primary cause of the disease namely impaired drainage through the trabecular meshwork. Therefore they only delay, but will not be able to inhibit the progressive loss of vision throughout the years. Furthermore, the pressure lowering effects of the drugs currently in use will often after months or years be insufficient resulting in a necessity for the administration of multiple drugs with increased risk of adverse effects and increased costs and inconvenience for the patient.

Treister et al., Intraocular Pressure and Outflow Facility, Arch. Ophthal., Vol. 83, pp. 311–318 (March 1970) disclose that the continuous oral treatment of normal women with mestranol (estrogen) causes a gradual decrease in IOP (Intraocular Pressure). Meyer et al., Influence of Norethynodret With Mestranol on Intraocular Pressure in Glaucoma, Arch. Ophthal., Vol. 75, pp 771–773 (June 1966) disclose that oral administration of mestranol with norethynodrel to patients with primary open angle glaucoma reduces IOP. Fotsis et al., The Endogenous Oestrogen Metabolite 2-Methoxyoestradiol Inhibits Angiogenesis and Suppresses Tumour Growth, Letters to Nature, Vol. 368, pp. 237–239 (Mar. 17, 1994) disclose that 2-methoxyoestradiol, an endogenous oestrogen metabolite, inhibits angiogenesis. U.S. Pat. No. 4,876,250 discloses that there may be a correlation between angiostatic activity and IOP lowering activity. U.S. Pat. No. 5,521,168.discloses the use of estrogen metabolites to lower intraocular pressure. DK 163.865B discloses the use of estrogens to treat increased pressure in the eye.

Many of the above mentioned compounds which have been found to lower intraocular pressure also have hormonal activity. It would be useful to have compounds which can be used to lower intraocular pressure without exhibiting any hormonal activity.

The compound 6-hydroxy-2-(4-hydroxyphenyl)benzo[b]thien-3-yl4-[2-(piperidin-1-yl)-ethoxyphenyl]methanone, hereinafter designated raloxifene, is a drug, known to have various pharmacological and physiological activities.

One object of the present invention is to provide compounds which can effectively be used for lowering intraocular pressure.

BRIEF DESCRIPTION OF THIS INVENTION

This invention provides the use of a compound of formula I

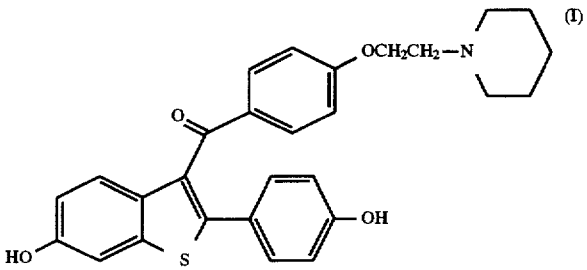

or a pharmaceutically and/or physiologically acceptable salt or solvate thereof for the manufacture of a pharmaceutical composition for lowering intraocular pressure.

DETAILED DESCRIPTION OF THIS INVENTION

Thus, the present invention provides the use of raloxifene of formula I or a pharmaceutically and/or physiologically acceptable salt or solvate thereof for the manufacture of a pharmaceutical composition useful for lowering and controlling intraocular pressure.

Within the present invention, compounds of formula I or a pharmaceutically and/or physiologically acceptable salt or solvate thereof as stated in claim 1 are used for lowering intraocular pressure in a patient e.g. associated with glaucoma or ocular hypertension. The present invention furthermore provides the use of a compound of above formula I or a pharmaceutically and/or physiologically acceptable salt or solvate thereof for the treatment or prevention of glaucoma or ocular hypertension. The methods of use provided by this invention are practised by administering to a human in need thereof a dose of a compound of formula I or a pharmaceutically and/or physiologically acceptable salt or solvate thereof, that is effective to reduce ocular pressure. The effect on ocular hypertension contemplated by the present invention includes both medical therapeutic treatment and/or prophylactic treatment as appropriate.

Raloxifene is synthesized according to known methods, such as Charles D. Jones, Mary G. Jevnikar, Andrew J. Pike, Mary K. Peters, Larry J. Black, Allen R. Thompson, Julie F. Falcone and James A. Clemens in J Med Chem 1984; 27: 1057–1066.

Within the present invention pharmaceutically and physiologically acceptable salts are salts with non-toxic acids, either inorganic acids such as hydrochloric acid, sulphuric acid and phosphoric acid, or organic acids such as formic acid, acetic acid, propionic acid, succinic acid, gluconic acid, lactic acid, citric acid, ascorbic acid, benzoic acid, embonic acid, methanesulphonic acid and malonic acid. A preferred salt is the hydrochloride salt.

Raloxifene and its salts are useful within human and veterinary medicine, for example, in the treatment of patients suffering from incresed intraocular pressure. For use within the present invention, raloxifene and its pharmaceutically acceptable salts are formulated with a pharmaceutically acceptable carrier to provide a medicament for topical, parenteral, oral, nasal, rectal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc. One skilled in this art may formulate the compounds in an appropriate manner, and in accordance with accepted practices, such as those disclosed in *Remington's Pharmaceutical Sciences*, Gennaro, ed., Mack Publishing Co., Easton, Pa., 1990.

The route of administration may be any route which effectively transfers the active compound to the appropriate or desired site of action. In the context of this invention raloxifene may especially be administered topically, perorally, or dermally. Doses are chosen in a range from 0.01 to 100 mg raloxifene per kg body weight per 24 hours, preferably in a range from 0.01 to 10 mg raloxifene per kg body weight per 24 hours.

The active compound can be formulated in any suitable ophthalmic formulation such as solutions, suspensions, ointments, etc. The formulations can include other components known to those skilled in the art of formulating ophthalmic products. For example, the formulations can include ophthalmically acceptable preservatives, surfactants, viscosity enhancers, penetration enhancers, and buffers. The formulations are applied topically to the eye of a mammal suffering from glaucoma or ocular hypertension according to the routine discretion of a skilled clinician.

Peroral administration is also preferred. Thus, the active compound is prepared in a form suitable for oral administration, such as a tablet or capsule. Typically, a pharmaceutically acceptable salt of the compound is combined with a carrier and molded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions are administered one or more times per day or week. An effective amount of such a pharmaceutical composition is the amount that provides a clinically significant effect against incresed intraocular pressure.

Such amounts will depend, in part, on the particular condition to be treated, age, weight, and general health of the patient, and other factors evident to those skilled in the art.

The pharmaceutical compositions may be administered in unit dosage form one or more times per day or week. In the alternative, they may be provided as controlled release formulations suitable for dermal implantation or as dermal patch. Said implants or patches are formulated to provide release of the active compound over the desired period of time, which can be up to several months or years. Controlled-release formulations are disclosed by, for example, Sanders et al., *J. Pharm Sci* 73 (1964), 1294–1297, 1984; U.S. Pat. No. 4,489,056; and U.S. Pat. No. 4,210,644, which are incorporated herein by reference.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLE 1

Twenty-four sexually mature female New Zealand White rabbits weighing between 3 and 5 kg each are divided into groups of six and the intraocular pressure is determined by tonometry in both eyes of each animal. One group is kept as a control group and is treated topically with vehicle alone. In the remaining groups of rabbits both eyes are treated daily topically for two weeks with 0.1% dexamethasone. Dexamethasone instillation results in an increased intraocular pressure in both eyes (corticosteroid-induced glaucoma, PA Knepper et al. Exp Eye Res 27: 567, 1978). Intraocular pressure is determined twice weekly during the experiment. After two weeks of treatment with dexamethasone the intraocular pressure is determined and treatment with the test substances is started in three groups. Test substances are dissolved in oil containing dexamethasone. The first group is treated with 17β-estradiol (1%). The second is treated with the raloxifene (5%) while the third group serve as a control and is treated with dexamethasone alone. All treatments are given topically once daily for 5 weeks.

Besides measurements of intraocular pressure twice weekly body weight is recorded once weekly.

At the end of the experiment the animals are sacrificed and an autopsy is performed. The eyes are dissected, the canal of Schlemm is localised and a sample of the trabecular meshwork is secured and frozen in vials on dry ice for biochemical determination of contents of proteoglycans. Furthermore, the uterus is isolated, gently blotted dry and weighed. The uterus weight is recorded.

EXAMPLE 2

The experiment described in example 1 is repeated in all substantially details except that sexually mature male New Zealand White rabbits are used and that the testes are isolated and weighed after the animals have been sacrificed.

We claim:

1. A method for lowering intraocular pressure, comprising adminstering to a patient an effective amount of a compound of the formula

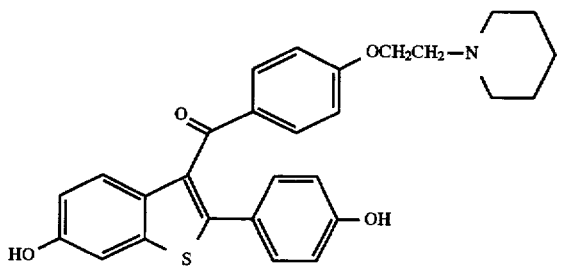

or a pharmaceutically and/or physiologically acceptable salt or solvate thereof.

2. The method according to claim 1 wherein said salt is the hydrocloride salt.

3. The method according to claim 1 wherein the compound is administered orally.

4. The method according to claim 1 wherein said compound is administered as a dose in a range from about 0.01 to 100 mg per kg body weight per 24 hours, preferably in the range from about 0.01 to 10 mg per kg body weight per 24 hours.

5. The method according to claim 1 wherein the compound is administered topically to the eye.

6. The method according to claim 1 wherein the compound is administered dermally.

7. The method according to claim 1 wherein said composition is administered one or more times per day or week.

* * * * *

UNITED STATES PATENT AND TRADEMARK OFFICE
CERTIFICATE OF CORRECTION

PATENT NO. : 5,798,369
DATED : August 25, 1998
INVENTOR(S) : Korsgaard et al.

It is certified that error appears in the above-identified patent and that said Letters Patent is hereby corrected as shown below:

On the Title page, [22]: delete "July 7, 1997" and insert --July 8, 1997--

Col. 2, line 26: delete "5,521,168.discloses" and insert --5,521,168 discloses--

Col. 2, line 36: delete "thien-3-yl4" and insert --thien-3-yl-4--

Signed and Sealed this

First Day of June, 1999

*Attest:*

Q. TODD DICKINSON

*Attesting Officer*   *Acting Commissioner of Patents and Trademarks*